(12) United States Patent
Rubin et al.

(10) Patent No.: US 7,899,530 B2
(45) Date of Patent: *Mar. 1, 2011

(54) METHODS AND APPARATUS FOR TREATING FIBRILLATION AND CREATING DEFIBRILLATION WAVEFORMS

(75) Inventors: Leo Rubin, Suffern, NY (US); Chris A. Bonnerup, Alvin, TX (US); Edward A. Schroeppel, Lake Jackson, TX (US)

(73) Assignee: Intermedics Inc., St. Paul, MN (US)

( * ) Notice: Subject to any disclaimer, the term of this patent is extended or adjusted under 35 U.S.C. 154(b) by 264 days.

This patent is subject to a terminal disclaimer.

(21) Appl. No.: 12/035,369

(22) Filed: Feb. 21, 2008

(65) Prior Publication Data

US 2008/0147134 A1      Jun. 19, 2008

Related U.S. Application Data

(60) Continuation of application No. 10/811,178, filed on Mar. 26, 2004, now Pat. No. 7,349,735, which is a division of application No. 09/966,233, filed on Sep. 28, 2001, now Pat. No. 6,757,561, which is a division of application No. 09/371,279, filed on Aug. 10, 1999, now Pat. No. 6,298,266.

(51) Int. Cl.
*A61N 1/00* (2006.01)
(52) U.S. Cl. .......................................................... 607/5
(58) Field of Classification Search ................. 607/4–8
See application file for complete search history.

(56) References Cited

U.S. PATENT DOCUMENTS

| | | |
|---|---|---|
| 4,768,512 A | 9/1988 | Imran |
| 4,800,883 A | 1/1989 | Winstrom |
| 5,184,616 A | 2/1993 | Weiss |
| 5,222,492 A | 6/1993 | Morgan et al. |
| 5,489,293 A | 2/1996 | Pless et al. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,693,952 A | 12/1997 | Cox |
| 5,716,381 A | 2/1998 | Reggiardo |
| 5,725,560 A | 3/1998 | Brink |
| 5,735,879 A | 4/1998 | Gliner et al. |

(Continued)

FOREIGN PATENT DOCUMENTS

EP      0280526      8/1988

OTHER PUBLICATIONS

"U.S. Appl. No. 09/371,279 Non-Final Office Action mailed Jan. 19, 2001", 11 pgs.

(Continued)

*Primary Examiner*—Scott M Getzow
(74) *Attorney, Agent, or Firm*—Schwegman, Lundberg & Woessner, P.A.

(57) ABSTRACT

Methods and apparatus for treating fibrillation utilize biphasic waveforms. A cardiac stimulator includes a defibrillation circuit that uses a pulse width modulated capacitive discharge to generate various biphasic waveforms, one or more of which may be delivered to the heart to treat the fibrillation.

21 Claims, 11 Drawing Sheets

U.S. PATENT DOCUMENTS

| | | | |
|---|---|---|---|
| 5,749,904 | A | 5/1998 | Gliner et al. |
| 5,749,905 | A | 5/1998 | Gliner et al. |
| 5,776,166 | A | 7/1998 | Gliner et al. |
| 5,803,927 | A | 9/1998 | Cameron et al. |
| 5,830,236 | A | 11/1998 | Mouchawar et al. |
| 5,836,978 | A | 11/1998 | Gliner et al. |
| 5,849,031 | A | 12/1998 | Martinez et al. |
| 5,906,633 | A | 5/1999 | Mouchawar et al. |
| 5,908,443 | A | 6/1999 | Brewer et al. |
| 5,913,877 | A | 6/1999 | Kroll et al. |
| 5,974,339 | A | 10/1999 | Baker, Jr. et al. |
| 7,349,735 | B2 | 3/2008 | Rubin et al. |

OTHER PUBLICATIONS

"U.S. Appl. No. 09/371,279 Notice of Allowance mailed May 9, 2001", 3 pgs.

"U.S. Appl. No. 09/371,279 Response to Non-Final Office Action filed Apr. 18, 2001", 12 pgs.

"U.S. Appl. No. 09/966,233 Non-Final Office Action mailed Dec. 4, 2003", 8 pgs.

"U.S. Appl. No. 09/966,233 Notice of Allowance mailed Feb. 6, 2004", 5 pgs.

"U.S. Appl. No. 09/966,233 Response to Non-Final Office Action filed Jan. 16, 2004", 18 pgs.

"U.S. Appl. No. 09/966,233 Supplemental Notice of Allowability mailed May 10, 2004", 3 pgs.

"International Application No. PCT/US00/21832 International Preliminary Examination Report mailed Sep. 20, 2001", 6 pgs.

"International Application No. PCT/US00/21832 International Search Report mailed Feb. 7, 2001", 5 pgs.

"International Application No. PCT/US00/21832 International Written Opinion mailed Jul. 24, 2001", 6 pgs.

Cleland, B. G., "A Conceptual Basis for Defibrillation Waveforms", *PACE*, 19, (Aug. 1996), pp. 1186-1195.

Hillsley, R. E., et al., "Is the Second Phase of a Biphasic Defibrillation Waveform the Defibrillating Phase?", *PACE*, 16, (Jul. 1993), pp. 1401-1411.

Jones, J. L., et al., "Cellular Excitation With High-Frequency Chopped Defibrillator Waveforms", *IEEE*, (1994), pp. 17-18.

Natale, A., et al., "Relative Efficacy of Different Tilts With Biphasic Defibrillation in Humans", *PACE*, 19, (Feb. 1996), pp. 197-206.

Sweeney, R. J., et al., "Defibrillation Using a High-Frequency Series of Monophasic Rectangular Pulses: Observation and Model Predictions", *Journal of Cardiovascular Electrophysiology*, 7, (Feb. 1996), 134-143.

"U.S. Appl. No. 10/811,178, Final Office Action mailed Jun. 4, 2007", 4 pgs.

"U.S. Appl. No. 10/811,178, Non-Final Office Action mailed Dec. 19, 2006", 5 pgs.

"U.S. Appl. No. 10/811,178, Notice of Allowance mailed Oct. 25, 2007", 4 pgs.

"U.S. Appl. No. 10/811,178, Preliminary Amendment filed Mar. 26, 2004", 16 pgs.

"U.S. Appl. No. 10/811,178, Response filed Mar. 19, 2007 to Non-Final Office Action mailed Dec. 19, 2006", 17 pgs.

"U.S. Appl. No. 10/811,178, Response filed Aug. 6, 2007 to Final Office Action mailed Jun. 4, 2007", 17 pgs.

METHODS AND APPARATUS FOR TREATING FIBRILLATION AND CREATING DEFIBRILLATION WAVEFORMS

This application is a Continuation of U.S. patent application Ser. No. 10/811,178, filed on Mar. 26, 2004, now issued as U.S. Pat. No. 7,349,735, which is a division of U.S. patent application Ser. No. 09/966,233, filed on Sep. 28, 2001, now issued as U.S. Pat. No. 6,757,561, which is a division of U.S. patent application Ser. No. 09/371,279, filed Aug. 10, 1999, now issued as U.S. Pat. No. 6,298,266, the specifications of which are incorporated herein by reference.

BACKGROUND OF THE INVENTION

1. Field of the Invention

The present invention relates generally to cardiac stimulators and, more particularly, to cardiac stimulators having the ability to treat fibrillations.

2. Description of the Related Art

This section is intended to introduce the reader to various aspects of art which may be related to various aspects of the present invention which are described and/or claimed below. This discussion is believed to be helpful in providing the reader with background information to facilitate a better understanding of the various aspects of the present invention. Accordingly, it should be understood that these statements are to be read in this light, and not as admissions of prior art.

As most people are aware, the human heart is an organ having four chambers. A septum divides the heart in half, with each half having two chambers. The upper chambers are referred to as the left and right atria, and the lower chambers are referred to as the left and right ventricles. Deoxygenated blood enters the right atrium through the inferior and superior vena cava. Contraction of the right atrium and of the right ventricle pump the deoxygenated blood through the pulmonary arteries to the lungs where the blood is oxygenated. This oxygenated blood is carried to the left atrium by the pulmonary veins. From this cavity, the oxygenated blood passes to the left ventricle and is pumped to a large artery, the aorta, which delivers the pure blood to the other portions of the body through the various branches of the vascular system.

In the normal human heart, the sinus node (generally located near the junction of the superior vena cava and the right atrium) constitutes the primary natural pacemaker by which rhythmic electrical excitation is developed. The cardiac impulse arising from the sinus node is transmitted to the two atrial chambers. In response to this excitation, the atria contract, pumping blood from those chambers into the respective ventricles. The impulse is transmitted to the ventricles through the atrioventricular (AV) node to cause the ventricles to contract. This action is repeated in a rhythmic cardiac cycle in which the atrial and ventricular chambers alternately contract and pump, then relax and fill. One-way valves between the atrial and ventricular chambers in the right and left sides of the heart and at the exits of the right and left ventricles prevent backflow of the blood as it moves through the heart and the circulatory system.

The sinus node is spontaneously rhythmic, and the cardiac rhythm originating from the sinus node is referred to as sinus rhythm. This capacity to produce spontaneous cardiac impulses is called rhythmicity. Some other cardiac tissues also possess this electrophysiologic property and, hence, constitute secondary natural pacemakers. However, the sinus node is the primary pacemaker because it has the fastest spontaneous rate and because the secondary pacemakers tend to be inhibited by the more rapid rate at which impulses are generated by the sinus node.

The resting rates at which sinus rhythm occurs in normal people differ from age group to age group, generally ranging between 110 and 150 beats per minute ("bpm") at birth, and gradually slowing in childhood to the range between 65 and 85 bpm usually found in adults. The resting sinus rate, typically referred to simply as the "sinus rate," varies from one person to another and, despite the aforementioned usual adult range, is generally considered to lie anywhere between 60 and 100 bpm (the "sinus rate range") for the adult population.

A number of factors may affect the sinus rate, and some of those factors may slow or accelerate the rate sufficiently to take it outside of the sinus rate range. Slow rates (below 60 bpm) are referred to as sinus bradycardia, and high rates (above 150 bpm) are referred to as sinus tachycardia. In particular, sinus tachycardia observed in healthy people arises from various factors which may include physical or emotional stress, such as exercise or excitement, consumption of beverages containing alcohol or caffeine, cigarette smoking, and the ingestion of certain drugs. The sinus tachycardia rate usually ranges between 101 and 160 bpm in adults, but has been observed at rates up to (and in infrequent instances, exceeding) 200 bpm in younger persons during strenuous exercise.

Sinus tachycardia is sometimes categorized as a cardiac arrhythmia, since it is a variation from the normal sinus rate range. Arrhythmia rates which exceed the upper end of the sinus rate range are termed tachyarrhythmias. Healthy people usually experience a gradual return to their normal sinus rate after the removal of the factors giving rise to sinus tachycardia. However, people suffering from disease may experience abnormal arrhythmias that may require special, and in some instances immediate, treatment. In this text, we typically refer to abnormally high rates that have not yet been determined to be caused by myocardial malfunction as tachycardias and to abnormally high rates that have been determined to be caused by myocardial malfunction as tachyarrhythmias.

It should also be appreciated that an abnormal tachyarrhythmia may initiate fibrillation. Fibrillation is a tachyarrhythmia characterized by the commencement of completely uncoordinated random contractions by sections of conductive cardiac tissue of the affected chamber, quickly resulting in a complete loss of synchronous contraction of the overall mass of tissue and a consequent loss of the blood-pumping capability of that chamber.

In addition to rhythmicity, other electrophysiologic properties of the heart include excitability and conductivity. Excitability, which is the property of cardiac tissue to respond to a stimulus, varies with the different periods of the cardiac cycle. As one example, the cardiac tissue is not able to respond to a stimulus during the absolute refractory phase of the refractory period, which is approximately the interval of contraction from the start of the QRS complex to the commencement of the T wave of the electrocardiogram. As another example, the cardiac tissue exhibits a lower than usual response during another portion of the refractory period constituting the initial part of the relative refractory phase, which is coincident with the T wave. Also, the excitability of the various portions of the cardiac tissue differs according to the degree of refractoriness of the tissue.

Similarly, the different portions of the heart vary significantly in conductivity, which is a related electrophysiologic property of cardiac tissue that determines the speed with which cardiac impulses are transmitted. For example, ventricular tissue and atrial tissue are more conductive than AV junction tissue. The longer refractory phase and slower conductivity of the AV junction tissue give it a significant natural protective function, as described in more detail later.

For a variety of reasons, a person's heart may not function properly and, thus, endanger the person's well-being. Most typically, heart disease affects the rhythmicity of the organ, but it may also affect the excitability and/or conductivity of the cardiac tissue as well. As most people are aware, medical devices have been developed to facilitate heart function in such situations. For instance, if a person's heart does not beat properly, a cardiac stimulator may be used to provide relief. A cardiac stimulator is a medical device that delivers electrical stimulation to a patient's heart. A cardiac stimulator generally includes a pulse generator for creating electrical stimulation pulses and a conductive lead for delivering these electrical stimulation pulses to the designated portion of the heart. As described in more detail below, cardiac stimulators generally supply electrical pulses to the heart to keep the heart beating at a desired rate, although they may supply a relatively larger electrical pulse to the heart to help the heart recover from fibrillation.

Early pacemakers were devised to treat bradycardia. These pacemakers did not monitor the condition of the heart. Rather, early pacemakers simply provided stimulation pulses at a fixed rate and, thus, kept the heart beating at that fixed rate. However, it was found that pacemakers of this type used an inordinate amount of energy due to the constant pulse production. Even the sinus node of a heart in need of a pacemaker often provides suitable rhythmic stimulation occasionally. Accordingly, if a heart, even for a short period, is able to beat on its own, providing an electrical stimulation pulse using a pacemaker wastes the pacemaker's energy.

To address this problem, pacemakers were subsequently designed to monitor the heart and to provide stimulation pulses only when necessary. These pacemakers were referred to as "demand" pacemakers because they provided stimulation only when the heart demanded stimulation. If a demand pacemaker detected a natural heartbeat within a prescribed period of time, typically referred to as the "escape interval", the pacemaker provided no stimulation pulse. Because monitoring uses much less power than generating stimulation pulses, the demand pacemakers took a large step toward conserving the limited energy contained in the pacemaker's battery.

Clearly, the evolution of the pacemaker did not cease with the advent of monitoring capability. Indeed, the complexity of pacemakers has continued to increase in order to address the physiological needs of patients as well as the efficiency, longevity, and reliability of the pacemaker. For instance, even the early demand pacemakers provided stimulation pulses, when needed, at a fixed rate, such as 72 pulses per minute. To provide a more physiological response, pacemakers having a programmably selectable rate were developed. So long as the heart was beating above this programmably selected rate, the pacemaker did not provide any stimulation pulses. However, if the heart rate fell below this programmably selected rate, the pacemaker sensed the condition and provided stimulation pulses as appropriate.

To provide even further physiological accuracy, pacemakers have now been developed that automatically change the rate at which the pacemaker provides stimulation pulses. These pacemakers are commonly referred to as "rate-responsive" pacemakers. Rate-responsive pacemakers sense a physiological parameter of the patient and alter the rate at which the stimulation pulses are provided to the heart. Typically, this monitored physiological parameter relates to the changing physiological needs of the patient. For instance, when a person is at rest, the person's heart need only beat relatively slowly to accommodate the person's physiological needs. Conversely, when a person is exercising, the person's heart tends to beat rather quickly to accommodate the person's heightened physiological needs.

Unfortunately, the heart of a person in need of a pacemaker may not be able to beat faster on its own. Prior to the development of rate-responsive pacemakers, patients were typically advised to avoid undue exercise, and pacemaker patients that engaged in exercise tended to tire quickly. Rate-responsive pacemakers help relieve this constraint by sensing one or more physiological parameters of a patient that indicates whether the heart should be beating slower or faster. If the pacemaker determines that the heart should be beating faster, the pacemaker adjusts its base rate upward to provide a faster pacing rate if the patient's heart is unable to beat faster on its own. Similarly, if the pacemaker determines that the patient's heart should be beating more slowly, the pacemaker adjusts its base rate downward to conserve energy and to conform the patient's heartbeat with the patient's less active state.

As noted above, pacemakers have historically been employed primarily for the treatment of heart rates which are unusually slow, referred to as bradyarrhythmias. However, over the past several years cardiac pacing has found significantly increasing usage in the management of heart rates which are unusually fast, referred to as tachyarrhythmias. Anti-tachyarrhythmia pacemakers take advantage of the previously mentioned inhibitory mechanism that acts on the secondary natural pacemakers to prevent their spontaneous rhythmicity, sometimes termed "postdrive inhibition" or "overdrive inhibition". In essence, the heart may be stimulated with a faster than normal pacing rate (1) to suppress premature atrial or ventricular contractions that might otherwise initiate ventricular tachycardia, flutter (a tachyarrhythmia exceeding 250 bpm), or fibrillation or (2) to terminate an existing tachyarrhythmia.

Typically, these pulses need only be of sufficient magnitude to stimulate the excitable myocardial tissue in the immediate vicinity of the pacing electrode. However, another technique for terminating tachyarrhythmias, referred to as cardioversion, utilizes apparatus to shock the heart synchronized to the tachyarrhythmia with one or more current or voltage pulses of considerably higher energy content than that of the pacing pulses. Defibrillation, a related technique, also involves applying one or more high energy "countershocks" to the heart in an effort to overwhelm the chaotic contractions of individual tissue sections to allow reestablishment of an organized spreading of action potential from cell to cell of the myocardium and, thus, restore the synchronized contraction of the mass of tissue.

In the great majority of cases, atrial fibrillation is hemodynamically tolerated and not life-threatening because the atria provide only a relatively small portion (typically on the order of 15 to 20 percent) of the total volume of blood pumped by the heart per unit time, typically referred to as cardiac output. During atrial fibrillation, the atrial tissue remains healthy because it is continuing to receive a fresh supply of oxygenated blood as a result of the continued pumping action of the ventricles. Atrial tachyarrhythmia may also be hemodynamically tolerated because of the natural protective property of the AV junctional tissue attributable to its longer refractory period and slower conductivity than atrial tissue. This property renders the AV junctional tissue unable to respond fully to the more rapid atrial contractions. As a result, the ventricle may miss every other, or perhaps two of every three, contractions in the high rate atrial sequence, resulting in 2:1 or 3:1

A-V conduction and, thus, maintain relatively strong cardiac output and an almost normal rhythm.

Nevertheless, in cases where the patient is symptomatic or at high risk in events of atrial tachyarrhythmia or fibrillation, special treatment of these atrial disorders may be appropriate. Such circumstances may include, for example, instances where the patient suffers from ventricular heart disease and cannot easily withstand even the small consequent reduction of ventricular pumping capability, as well as instances where the rapid atrial rhythm is responsible for an excessively rapid ventricular rate. The methods of treatment commonly prescribed by physicians for treating atrial tachyarrhythmia and fibrillation include medication, catheter ablation, pacing therapy, cardiac shock therapy, and in some cases, surgically creating an A-V block and implanting a ventricular pacemaker.

In contrast to the atrial arrhythmias discussed above, cardiac output may be considerably diminished during an episode of ventricular tachyarrhythmia because the main pumping chambers of the heart, the ventricles, are only partially filled between the rapid contractions of those chambers. As in the case atrial fibrillation, ventricular fibrillation is characterized by rapid, chaotic electrical and mechanical activity of the excitable myocardial tissue. However, in contrast to atrial fibrillation, ventricular fibrillation manifests an instantaneous cessation of cardiac output as the result of the ineffectual quivering of the ventricles—a condition that typically requires almost immediate treatment.

The type and shape of the defibrillation waveform, as well as its intensity, determine the efficacy of the waveform in treating fibrillation. For example, in older defibrillators, such as external devices used in emergency situations, a monophasic waveform was used. A typical monophasic waveform rises from zero volts to some prescribed positive voltage appropriate to defibrillate the heart. While such a waveform typically overcomes the fibrillation of the heart, if it is not of sufficient intensity refibrillation may occur.

To address this concern, most defibrillators now use a biphasic waveform. A typical biphasic waveform rises from zero volts to some prescribed positive voltage, and then switches rapidly to some prescribed negative voltage before returning to zero. Biphasic waveforms exhibit several advantages over monophasic waveforms. For example, because part of a biphasic waveform is at a positive voltage level and part is at a negative voltage level, a biphasic waveform tends to deliver a more balanced charge than a monophasic waveform. Because a more balanced charge leaves less net charge on the interface between the heart and the electrode, there is less polarization at this boundary. This is a desirable result because the polarization potential of a polarized boundary must first be overcome to deliver the required stimulation to the heart, thus increasing the required intensity of the waveform and the power drain on the cardiac stimulator. Therefore, biphasic waveforms typically require less energy to defibrillate than monophasic waveforms.

While biphasic waveforms appear to exhibit greater efficacy than monophasic waveforms, various problems still exist. For instance, theoretically speaking, biphasic waveforms may take virtually an infinite number of shapes. While a variety of biphasic waveforms have been considered for defibrillation, no known waveform appears to be best suited for every situation. Furthermore, many waveforms remain theoretical, because no circuit suitable for use in an implantable ICD has been designed to create the waveform.

The present invention may address one or more of the problems set forth above.

SUMMARY OF THE INVENTION

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a biphasic defibrillation waveform which includes a positive voltage phase beginning at about zero volts and having an initial positive voltage magnitude greater than zero volts. The positive voltage phase has a first positively sloped portion extending from the initial positive voltage magnitude to a maximum positive voltage magnitude greater than the initial positive voltage magnitude. A negative voltage phase has an initial maximum negative voltage magnitude less than zero volts extending from the maximum positive voltage magnitude of the positive voltage phase. The negative voltage phase has a second positively sloped portion extending from the initial maximum negative voltage magnitude to a terminal negative voltage magnitude greater than the initial maximum negative voltage magnitude.

In accordance with another aspect of the present invention, there is provided a biphasic defibrillation waveform which includes a positive voltage phase having an initial voltage magnitude equal to about zero volts and having a first positively sloped portion extending from the initial voltage magnitude to a maximum positive voltage magnitude greater than the initial voltage magnitude. A negative voltage phase has an initial negative voltage magnitude less than or equal to zero volts extending from the maximum positive voltage magnitude of the positive voltage phase. The negative voltage phase has a second sloped portion extending from the initial negative voltage magnitude to a terminal negative voltage having a magnitude less than or equal to zero volts.

In accordance with still another aspect of the present invention, there is provided a biphasic defibrillation waveform which includes a positive voltage phase having an initial maximum positive voltage magnitude greater than zero volts and having a first negatively sloped portion extending from the initial maximum positive voltage magnitude to a terminal positive voltage magnitude less than the initial maximum positive voltage magnitude. A negative voltage phase has an initial negative voltage magnitude less than or equal to zero volts extending from the terminal positive voltage magnitude of the positive voltage phase. The negative voltage phase has a second sloped portion extending from the initial negative voltage magnitude to a terminal negative voltage having a magnitude less than or equal to zero volts.

In accordance with yet another aspect of the present invention, there is provided a biphasic defibrillation waveform which includes a positive voltage phase having an initial positive voltage having a magnitude greater than or equal to zero volts and having a first sloped portion extending from the initial positive voltage to a terminal positive voltage having magnitude greater than or equal to zero volts. A negative voltage phase has an initial negative voltage having a magnitude less than or equal to zero volts extending from the terminal positive voltage of the positive voltage phase. The negative voltage phase has a second sloped portion extending from the initial negative voltage to a terminal negative voltage having a magnitude less than or equal to zero volts.

In accordance with a further aspect of the present invention, there is provided a method of generating a biphasic defibrillation waveform that includes the acts of: generating a positive voltage phase having an initial positive voltage having a magnitude greater than or equal to zero volts and having a first sloped portion extending from the initial positive voltage to a terminal positive voltage having magnitude greater than or equal to zero volts; and generating a negative voltage phase having an initial negative voltage having a magnitude less than or equal to zero volts extending from the terminal positive voltage of the positive voltage phase, the negative voltage phase having a second sloped portion extending from the initial negative voltage to a terminal negative voltage having a magnitude less than or equal to zero volts.

In accordance with a still further aspect of the present invention, there is provided a defibrillation waveform generator that includes: an arrhythmia detector adapted to be coupled to a heart, the arrhythmia detector delivering a detection signal in response to detecting fibrillation in the heart; a charging circuit coupled to a capacitor, the charging circuit charging the capacitor to a given voltage; a controller operably coupled to the arrhythmia detector to receive the detection signal, the controller delivering a first control signal, a second control signal, and a third control signal in response to receiving the detection signal; a voltage-to-frequency convertor coupled to the controller to receive the first control signal, the voltage-to-frequency convertor delivering a frequency signal having a frequency correlative to the first control signal; a pulse width modulator coupled to the controller to receive the second control signal and coupled to the voltage-to-frequency convertor to receive the frequency signal, the pulse width modulator delivering a pulse width modulated signal having a frequency correlative to the frequency signal and having a duty cycle correlative to the second control signal; and a switching circuit adapted to be coupled between the capacitor and the heart, the switching circuit being coupled to the controller to receive the third control signal and to the pulse width modulator to receive the pulse width modulated signal, the switching circuit controllably discharging the capacitor across the heart to deliver a defibrillation waveform in response to the third control signal and the pulse width modulated signal.

In accordance with a yet further aspect of the present invention, there is provided a defibrillation waveform generator that includes: an arrhythmia detector adapted to be coupled to a heart, the arrhythmia detector delivering a detection signal in response to detecting fibrillation in the heart; a charging circuit coupled to a first capacitor and to a second capacitor, the charging circuit charging the first capacitor and the second capacitor to a respective given voltage; a controller operably coupled to the arrhythmia detector to receive the detection signal, the controller delivering a first control signal, a second control signal, and a third control signal in response to receiving the detection signal; a voltage-to-frequency convertor coupled to the controller to receive the first control signal, the voltage-to-frequency convertor delivering a frequency signal having a frequency correlative to the first control signal; a pulse width modulator coupled to the controller to receive the second control signal and coupled to the voltage-to-frequency converter to receive the frequency signal, the pulse width modulator delivering a pulse width modulated signal having a frequency correlative to the frequency signal and having a duty cycle correlative to the second control signal; and a switching circuit adapted to be coupled between the first and second capacitors and the heart, the switching circuit being coupled to the controller to receive the third control signal and to the pulse width modulator to receive the pulse width modulated signal, the switching circuit controllably discharging the first capacitor across the heart to deliver a positive phase defibrillation waveform in response to the third control signal and the pulse width modulated signal, and the switching circuit controllably discharging the second capacitor across the heart to deliver a negative phase defibrillation waveform in response to the third control signal and the pulse width modulated signal.

In accordance with another aspect of the present invention, there is provided a cardiac stimulator for treating fibrillations. The cardiac stimulator includes an implantable case containing: an atrial sensing circuit adapted to deliver an atrial signal correlative to a condition of an atrium of a heart; a ventricular sensing circuit adapted to deliver a ventricular signal correlative to a condition of a ventricle of the heart; an inductor-less pulse generator adapted to deliver pulse width modulated electrical stimulation to the ventricle; and a control circuit coupled to the ventricular sensing circuit to receive the ventricular signal, the control circuit directing the pulse generator to deliver pulse width modulated electrical stimulation to the ventricle in response to classifying a ventricular tachyarrhythmia as a fibrillation.

In accordance with still another aspect of the present invention, there is provided a cardiac stimulator that includes: means for determining whether a fibrillation exists in a ventricle; means for charging at least one capacitor; and means for discharging the at least one capacitor in a pulse width modulated manner to the ventricle to create a defibrillation waveform for treating the fibrillation.

In accordance with yet another aspect of the present invention, there is provided a method of treating fibrillation that includes the acts of: (a) determining whether a fibrillation exists in a ventricle; (b) charging at least one capacitor; and (c) electrically stimulating the ventricle with a waveform to treat the fibrillation by discharging the at least one capacitor in a pulse width modulated manner.

BRIEF DESCRIPTION OF THE DRAWINGS

The foregoing and other advantages of the invention will become apparent upon reading the following detailed description and upon reference to the drawings in which.

DESCRIPTION OF SPECIFIC EMBODIMENTS

Figure 1:
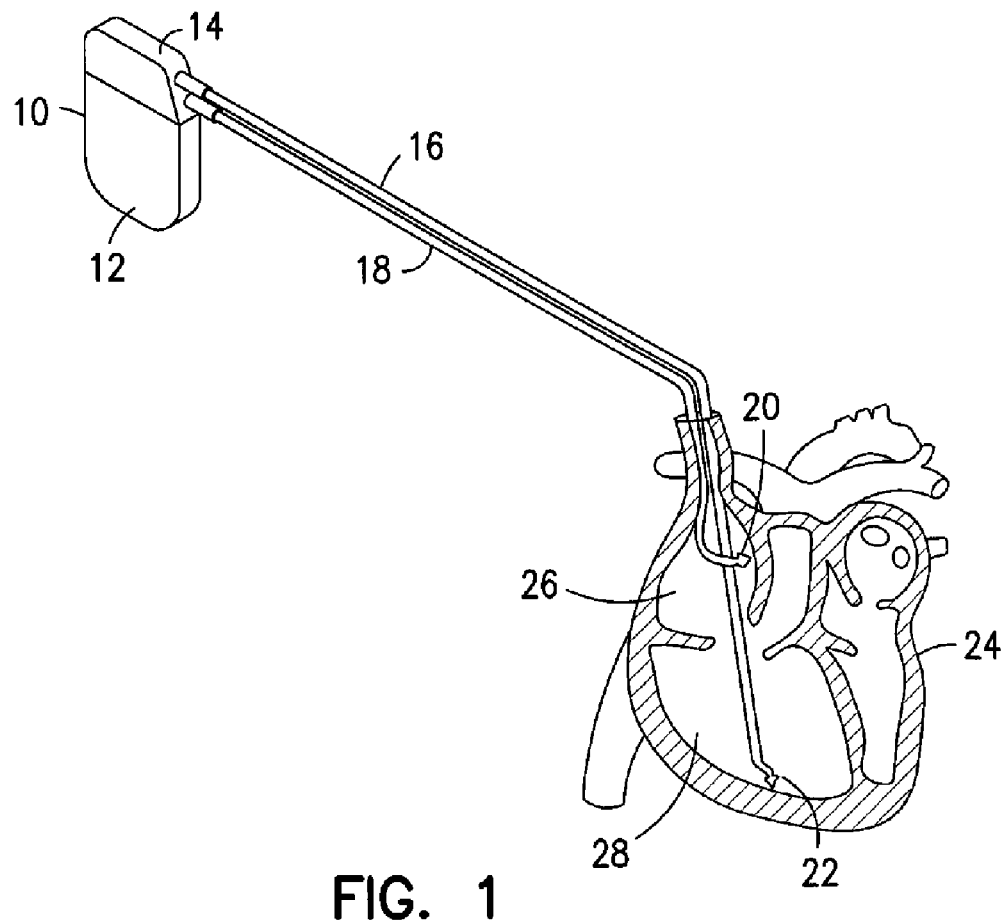
FIG. 1 illustrates a cardiac stimulator having two leads coupled to a patient's heart.

Turning now to the drawings, and referring initially to FIG. 1, one embodiment of a dual-chamber cardiac stimulator is illustrated and generally designated by the reference numeral 10. As discussed below, the cardiac stimulator 10 advantageously includes a defibrillator circuit that produces one or more waveforms for treating a detected fibrillation. The general structure and operation of the cardiac stimulator 10 will be discussed with reference to FIGS. 1-3. Then, various waveforms for treating fibrillation will be discussed with reference to FIGS. 4-32. Once these waveforms have been described, various exemplary methods and circuits for creating these waveforms will be described with reference to FIGS. 33-37.

As shown in FIG. 1, the body of the cardiac stimulator 10 includes a case 12 and a header 14. The cardiac stimulator 10 may be implantable or non-implantable. If implantable, the case 12 and the header 14 are hermetically sealed to prevent bodily fluids from damaging the internal circuitry of the cardiac stimulator 10. Typically, the case 12 is made of titanium, and the header 14 is made of polyethylene.

In the described embodiment, the cardiac stimulator 10 is a dual chamber cardioverter/defibrillator (ICD), although it should be understood that the teachings set forth herein may apply to other types of cardiac stimulators, such as an implantable defibrillator or an external, stand-alone defibrillator for example. Because the cardiac stimulator 10 is a dual chamber ICD, it includes an atrial lead 16 and a ventricular lead 18. Typically, the leads 16 and 18 are generally flexible and include an electrically conductive core surrounded by a protective sheath. For instance, the internal core may be a coiled wire of titanium, and the protective sheath may be a coating of polyurethane or silicone.

Each lead 16 and 18 includes a respective tip 20 and 22 that is designed to be implanted or coupled to an interior surface of a chamber of the heart 24. As illustrated, the tip 20 of the atrial lead 16 is implanted in an inner wall of the right atrium 26 of the heart 24 for sensing and/or stimulating the right atrium 26. Similarly, the tip 22 of the ventricular lead 18 is implanted in an inner wall of the right ventricle 28 of the heart 24 for sensing and/or stimulating the right ventricle 28.

Figure 2:
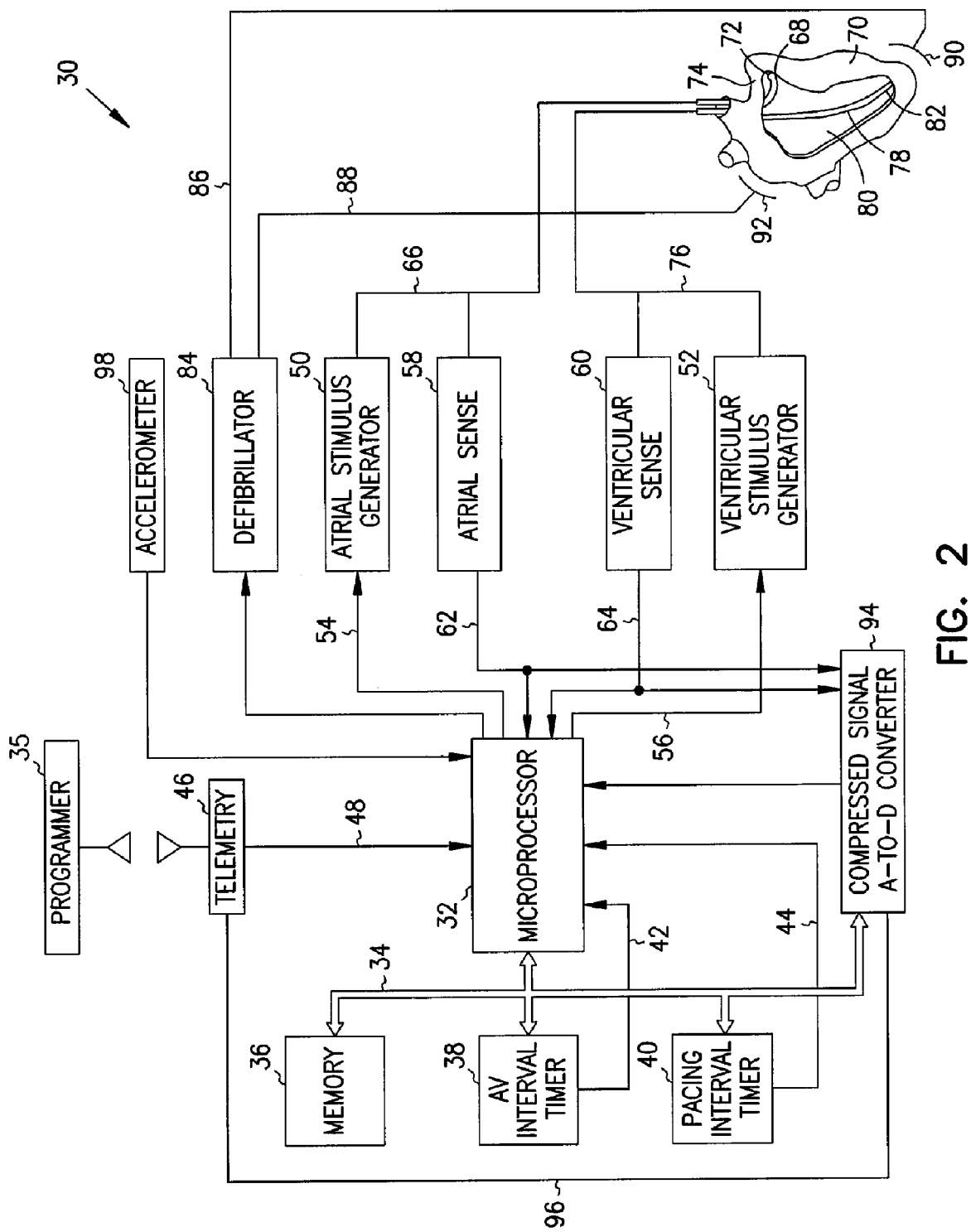
FIG. 2 illustrates a block diagram of one embodiment of a cardiac stimulator's circuitry in accordance with the present invention.

The cardiac stimulator 10 uses electronic circuitry to perform its functions, such as the circuitry illustrated in FIG. 2 and generally designated by the reference numeral 30. A microprocessor 32 provides pacemaker control and computational facilities. Although it will be appreciated that other forms of circuitry, such as analog or discrete digital circuitry, can be used in place of microprocessor 32, a microprocessor is typically advantageous due to its miniature size and its flexibility. Energy efficient microprocessors, which are designed specifically for use in pacemakers, are particularly advantageous.

The microprocessor 32 has input/output ports connected in a conventional manner via bidirectional bus 34 to memory 36, an AV interval timer 38, and a pacing interval timer 40. In addition, the AV interval timer 38 and pacing interval timer 40 each has an output connected to a corresponding input port of the microprocessor 32 by lines 42 and 44 respectively. Memory 36 may include both ROM and RAM, and the microprocessor 32 may also contain additional ROM and RAM. The pacemaker operating routine is typically stored in ROM, while the RAM stores programmable parameters and variables in conjunction with the pacemaker operation.

The AV and pacing interval timers 38 and 40 may be external to the microprocessor 32, as illustrated, or internal thereto. The timers 38 and 40 may be, for instance, suitable conventional up/down counters of the type that are initially loaded with a count value and count up to or down from the value and output a roll-over bit upon completing the programmed count. The initial count value is loaded into the timers 38, 40 on bus 34 and the respective roll-over bits are output to the microprocessor 32 on lines 42 and 44.

The microprocessor 32 typically also has an input/output port connected to a telemetry interface 46 by line 48. The pacemaker, when implanted, is thus able to receive pacing and rate control parameters from an external programmer 35 and to send data to an external receiver if desired. Many suitable telemetry systems are known to those skilled in the art.

The microprocessor output ports are connected to inputs of an atrial stimulus pulse generator 50 and a ventricular stimulus pulse generator 52 by control lines 54 and 56, respectively. The microprocessor 32 transmits pulse parameter data, such as amplitude and width, as well as enable/disable and pulse initiation codes to the generators 50, 52 on the respective control lines. The microprocessor 32 also has input ports connected to outputs of an atrial sense amplifier 58 and a ventricular sense amplifier 60 by lines 62 and 64 respectively. The atrial and ventricular sense amplifiers 58, 60 detect occurrences of P-waves and R-waves respectively.

The input of the atrial sense amplifier 58 and the output of the atrial stimulus pulse generator 50 are connected to a first conductor 66 which is inserted in a first conventional lead 68. Lead 68 is inserted into a heart 70 intravenously or in any other suitable manner. The lead 66 has an electrically conductive pacing/sensing tip 72 at its distal end which is electrically connected to the conductor 66. The pacing/sensing tip 72 is typically lodged in the right atrium 74.

The input of the ventricular sense amplifier 60 and the output of the ventricular stimulus pulse generator 52 are connected to a second conductor 76. The second conductor 76 is inserted in a second conventional lead 78 which is inserted intravenously or otherwise in the right ventricle 80 of the heart 70. The second lead 78 has an electrically conductive pacing/sensing tip 82 at its distal end. The pacing/sensing tip 82 is electrically connected to the conductor 76. The pacing/sensing tip 82 is typically lodged on the wall of the right ventricle 80.

The conductors 66 and 76 conduct the stimulus pulses generated by the atrial and ventricular stimulus pulse generators 50, 52, respectively, to the pacing/sensing tips 72, 82. The pacing/sensing tips 72, 82 and corresponding conductors 66, 76 also conduct sensed cardiac electrical signals in the right atrium and right ventricle to the atrial and ventricular sense amplifiers 58, 60.

To provide defibrillation capability in the cardiac stimulator 10, a high voltage defibrillator circuit 84 is provided which is controlled by the microprocessor 32. The defibrillator circuit 84 is connected to heart tissue through two high voltage leads 86, 88 which communicate with the heart through electrodes 90, 92. In the illustrated embodiment, epicardial patch electrodes are diagrammatically represented. However, other electrode configurations, including endocardial electrodes, may also be suitable. In fact, certain leads may be suitable for delivering pacing pulses as well as defibrillation pulses, thus rendering the leads 86 and 88 and the electrodes 90 and 92 superfluous. One example of suitable leads is disclosed in U.S. Pat. No. 5,476,502, the entirety of which is hereby incorporated by reference.

The atrial and ventricular sense amplifiers 58, 60 communicate both with the microprocessor and with a compressed signal A-to-D converter 94. The compressed signal A-to-D converter 94 communicates through the bus 34 with memory 36 and the microprocessor 32, primarily, and on a line 96 with the telemetry 46. Thus, the output of the converter 94 can be manipulated by the microprocessor 32, or stored in memory 36 or directly communicated through the telemetry 46 to the programmer 35. The stored output of the convertor 94 may also be subsequently communicated from memory 36 through the telemetry 46 to the programmer 35.

The microprocessor 32 may also base its control on other parameters, such as information received from other sensors. For example, an activity sensor 98, such as an implanted accelerometer, may be used to gather information relating to changing environmental or physiological conditions. Although the use of an accelerometer as the activity sensor 98 may be advantageous, other types of sensors may also be used to gauge certain types of physical activity or physical condition, such as "displacement" sensors, temperature sensors, oxygen sensors, pH sensors, and/or impedance sensors. Indeed, when the dual-chamber cardiac stimulator 10 is operating in rate-responsive mode, the stimulator 10 typically adjusts the pacing rate in response to one or more detected physiological or environmental parameters correlated to a physiologic need.

Figure 3:
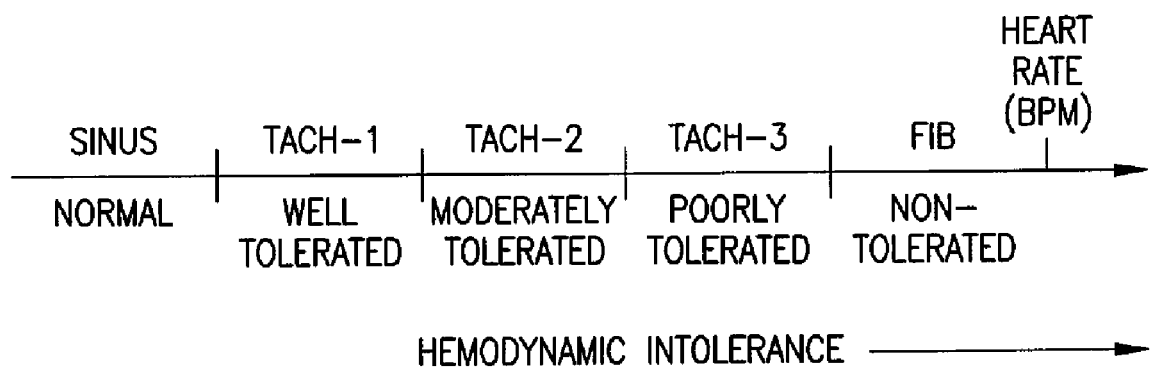
FIG. 3 illustrates a diagram of a heart rate spectrum that is partitioned into various arrhythmia classes.

The operation of the cardiac stimulator 10 may be affected by heart rate. With reference now to FIG. 3, a heart rate spectrum may be stored in the circuitry 30 and partitioned into a multiplicity of regions defining contiguous, successive heart rate ranges. At the lower end of the illustrated heart rate spectrum is normal rhythm, which is designated SINUS. As the heart rate rises along the spectrum, the spectrum enters progressively higher rate ranges associated with ventricular tachycardia or tachyarrhythmia, respectively labeled TACH-1, TACH-2, and TACH-3. Beyond the ventricular tachycardia ranges of the spectrum lies the range associated with ventricular fibrillation, which is labeled FIB.

It will be observed that the spectrum may be partitioned such that the rate ranges are representative of respective degrees of hemodynamic tolerance of the patient to cardiac rates in those regions. Generally speaking, heart rates in the SINUS region are normal, whereas rates in the FIB region cannot be tolerated. Furthermore, the ascending order of the three illustrated ventricular tachyarrhythmia regions TACH-1, TACH-2, and TACH-3 depicts well tolerated, moderately tolerated, and poorly tolerated classes of tachycardia, respectively. Although three tachyarrhythmia classes are illustrated, the actual number of such classes may be greater or fewer depending on the judgment of the physician regarding the management of arrhythmias and the prescription of therapy regimens for a particular patient. As will become clear from the discussion of therapy considerations below, the fibrillation range FIB is of particular concern for the purposes of this discussion.

Figure 4:
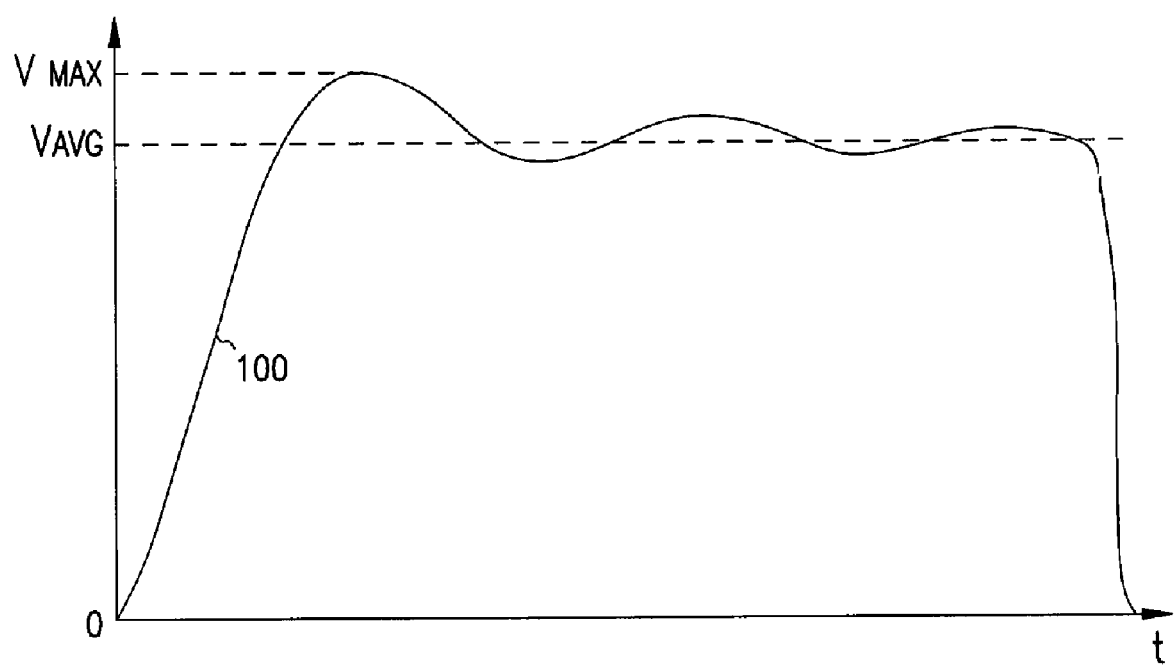
FIG. 4 illustrates a portion of a conventional monophasic defibrillation waveform.

When the cardiac stimulator 10 detects a heart rate in the fibrillation range FIB, the defibrillator circuit 84 generates one or more defibrillation waveforms that are delivered to the heart via the appropriate leads. The type, shape, and intensity of a defibrillation waveform are determinative of the efficacy of the treatment of the fibrillated heart. Regarding the type of waveform, the advantages of a biphasic waveform over a monophasic waveform have been discussed previously. To illustrate certain differences between these types of waveforms, a monophasic waveform 100 is illustrated in FIG. 4.

As can be seen, a typical monophasic waveform rises from zero volts to a certain maximum voltage $V_{max}$ and exhibits a certain oscillatory characteristic about an average voltage $V_{avg}$ before returning to zero volts. As compared to the biphasic waveforms illustrated in the subsequent figures, the maximum voltage $V_{max}$ necessary for the monophasic waveform 100 to overcome the defibrillation threshold tends to be greater, possibly by fifty percent or more, than the maximum voltage of the various biphasic waveforms. As discussed previously, this problem is primarily due to the generation of a polarized boundary between the electrodes and the heart caused by the large net voltage delivery of the monophasic waveform 100.

However, the primary advantage of the monophasic waveform 100 is that it may be generated by capacitive discharge circuitry that is small enough to be used within an implantable cardiac stimulator. At present, the circuitry for producing suitable biphasic defibrillation waveforms typically utilizes a massive circuit containing a very large inductor to create the appropriately shaped waveforms. Such circuitry is not feasible for use in an implantable device.

Furthermore, the types of biphasic waveforms previously considered for use in treating fibrillation are somewhat limited and are not programmably selectable for treating various types of fibrillation. In the discussion below, various biphasic waveform components are described, as well as the various combinations of resulting biphasic waveforms. The nature of each of these waveforms will be discussed, along with exemplary situations in which certain waveforms may prove efficacious. Then, three exemplary circuits will be described for producing a variety of biphasic waveforms, including the illustrated biphasic waveforms.

Figure 5:
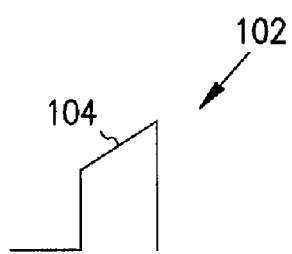
FIGS. 5-7 illustrate three positive voltage phase components of a biphasic waveform.
Figure 6:
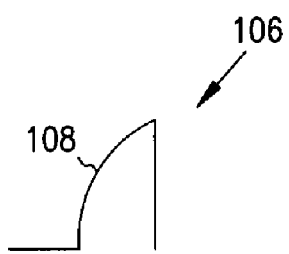
Figure 7:
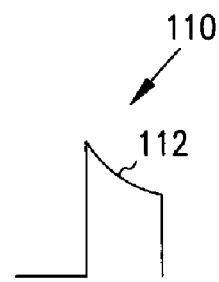

FIGS. 5-7 illustrate three different positive voltage components of a biphasic waveform that may be used for defibrillation. The positive voltage component 102 illustrated in FIG. 5 includes a linearly sloped portion 104. The linearly sloped portion 104 begins at some value greater than or equal to zero volts and rises in a linear fashion to a maximum voltage dependent upon the given slope and the duration of the positive phase of the waveform. It is believed that a positive voltage which ramps up to its maximum voltage may lower the defibrillation threshold, thus reducing the maximum voltage necessary to defibrillate the heart. Thus, the shape of the waveform component 102 may exhibit advantages over the monophasic waveform 100.

The waveform component 106 illustrated in FIG. 6 also ramps up to a maximum positive voltage. However, unlike the waveform component 102, the waveform component 106 includes a portion 108 which ramps upwardly with a variably decreasing slope. The portion 108 begins its rise at a voltage greater than or equal to zero volts and increases to its maximum voltage at the end of the positive phase. Given the same initial voltage, it should be appreciated that the waveform component 106 carries slightly more power than the waveform component 102.

Another variant of a positive voltage component of a biphasic waveform is illustrated in FIG. 7 as a waveform component 110. The waveform component 110 is illustrated as including a sloped portion 112 that decreases at an exponential rate from an initial maximum voltage to a final voltage that is greater than or equal to zero volts. It should be appreciated that the sloped portion 112 of the waveform component 110 alternatively may be positively sloped in an exponentially increasing fashion from an initial voltage that is greater than or equal to zero volts to some maximum voltage at the end of the phase.

It is currently believed that most patients will respond adequately to one or more of the waveform components 102, 106, and 110. Thus, in combination with the negative voltage phases described below with reference to FIGS. 8-13, a physician may program one or more defibrillation waveforms into the cardiac stimulator 10 to provide a patient with the most efficacious treatment.

Figure 8:
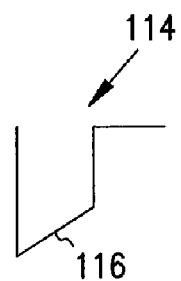
FIGS. 8-13 illustrate six negative voltage phase components of a biphasic waveform.
Figure 9:
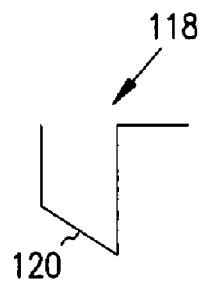
Figure 10:
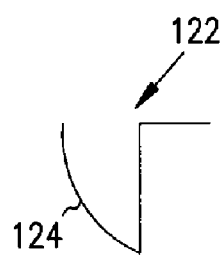
Figure 11:
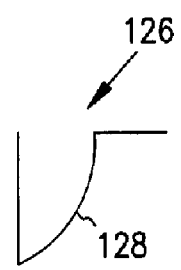
Figure 12:
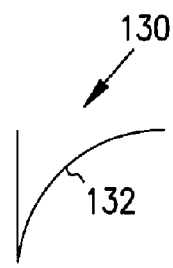
Figure 13:
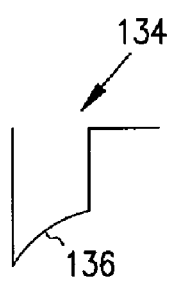
Figure 14:
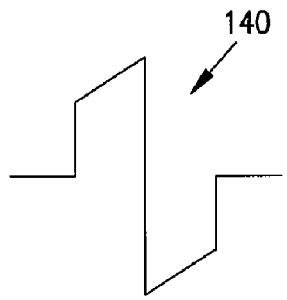
FIGS. 14-31 illustrate eighteen biphasic defibrillation waveforms created from combining the three positive voltage phase components illustrated in FIGS. 5-7 with the six negative voltage phase components illustrated in FIGS. 8-13.
Figure 15:
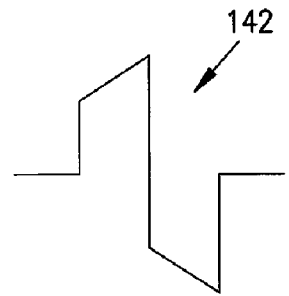
Figure 16:
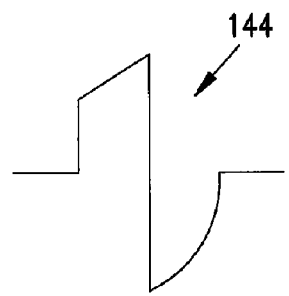
Figure 17:
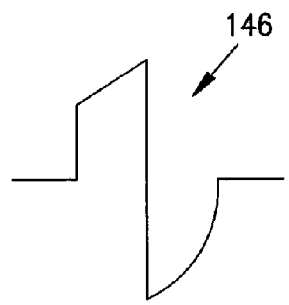
Figure 18:
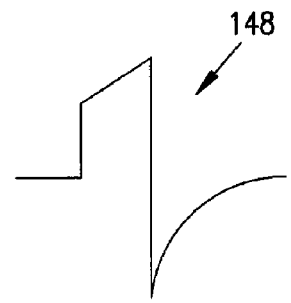
Figure 19:
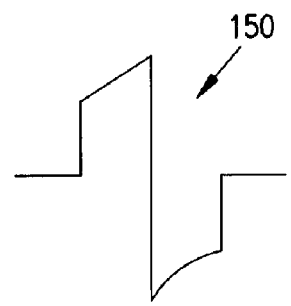
Figure 20:
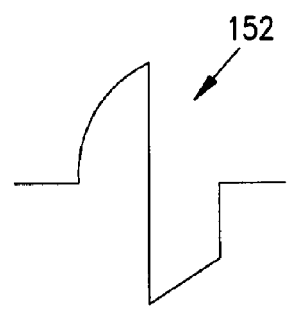
Figure 21:
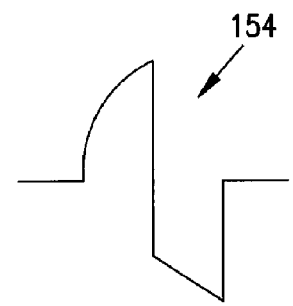
Figure 22:
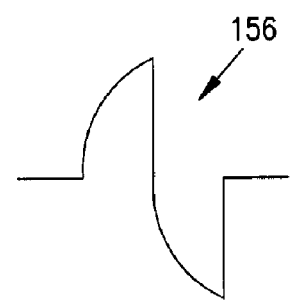
Figure 23:
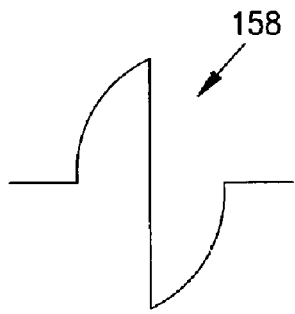
Figure 24:
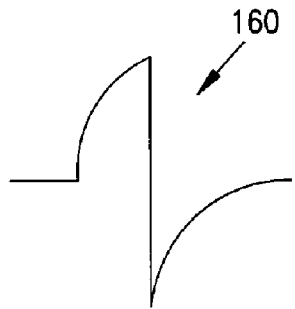
Figure 25:
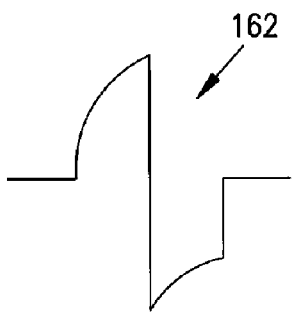
Figure 26:
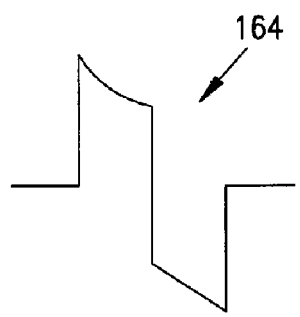
Figure 27:
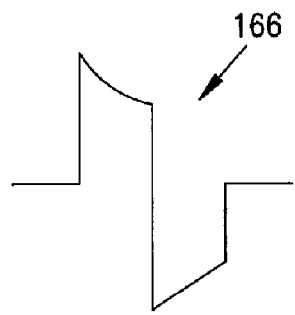
Figure 28:
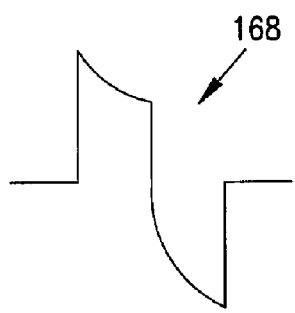
Figure 29:
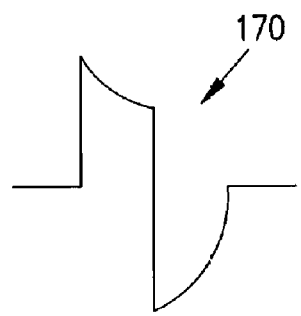
Figure 30:
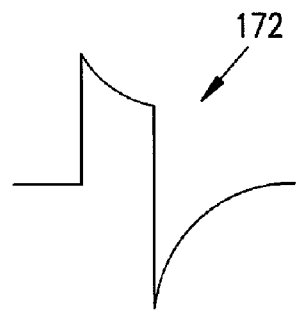
Figure 31:
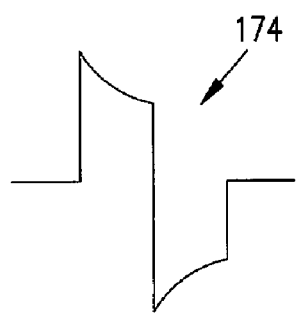

Various negative voltage waveform components are illustrated in FIGS. 8-13. As described in more detail below, these six negative voltage components may be combined with the three positive voltage components described above to form the eighteen waveforms illustrated in FIGS. 14-31. FIG. 8 illustrates a negative voltage waveform component 114. The component 114 includes a positively sloping portion 116 that increases at a linear rate from a maximum negative voltage to a smaller negative voltage that is less than or equal to zero volts. FIG. 9 illustrates a negative voltage waveform component 118 which includes a negatively sloping portion 120 that linearly decreases from an initial voltage less than or equal to zero volts to some maximum negative voltage. FIG. 10 illustrates a waveform 122 that includes a portion 124 that slopes negatively in an exponential manner from an initial voltage less than or equal to zero volts to a maximum negative voltage. FIG. 11 illustrates a waveform 126 that includes a portion 128 that slopes positively in an exponential manner from an initial maximum negative voltage to a smaller negative voltage less than or equal to zero volts. FIG. 12 illustrates a waveform 130 that includes a portion 132 that ramps upwardly with a variably decreasing slope from a maximum negative voltage to a smaller negative voltage less than or equal to zero volts. Finally, FIG. 13 illustrates a waveform 134 that includes a sloped portion 136 similar to the portion 132 where the final negative voltage is less than zero volts.

Referring additionally now to FIGS. 14-31, it can be seen that the waveforms 140-150 illustrated in FIGS. 14-19 are comprised of the positive voltage waveform component 102 in combination with the negative voltage waveform components 114, 118, 122, 126, 130, and 134, respectively. Similarly, the waveforms 152-162 illustrated in FIGS. 20-25 are composed of the positive voltage waveform component 106 in combination with the negative voltage waveform components 114, 118, 122, 126, 130, and 134, respectively, and the waveforms 164-174 illustrated in FIGS. 26-31 are composed of the positive voltage waveform component 110 in combination with the negative voltage waveform components 114, 118, 122, 126, 130, and 134, respectively.

Each of the waveforms 140-174 illustrated in the respective FIGS. 14-31 have certain advantages that may make a particular waveform advantageous for treating fibrillation. For example, the waveforms 140-162 have a positively sloped first phase. This slow ramp up of the positive voltage in the first phase tends to minimize polarization of the electrode-tissue interface and results in more efficient energy transfer. Using conventional techniques, the first phase of the waveforms 152-162 would be easier to generate than the first phase of the waveforms 140-150 using analog circuitry, primarily because the latter requires the use of an inductor. Similarly, the second phase of the waveforms 140, 142, 144, 152, 158, 156, 164, and 166 is more difficult to generate using conventional analog methods than the other waveforms because such generation requires the use of an inductor in the circuit. Conversely, using conventional techniques, the generation of the first phase of the waveforms 164-174 could be generated using a capacitive discharge. However, as will be explained in detail below, the presently disclosed circuits illustrated in FIGS. 34 and 35 can generate each of the waveforms 140-174 through the use of a capacitive discharge without the use of an inductor.

In regard to additional advantages, it should also be noted that the waveforms 140, 146, 148, 150, 152, 158, 160, and 162 have a large, abrupt gradient between the positive peak of the first phase and the negative peak of the second phase. This gradient typically promotes more effective defibrillation. Indeed, each of these waveforms has an ascending slope in the first phase followed by the large gradient. As the slope rises, by virtue of its capacitance (dV/dt), the tissue is prepared for the abrupt change in the amplitude and direction of the voltage which occurs between the two phases. Thus, these waveforms combine two advantageous characteristics leading to low defibrillation thresholds, i.e., a slow ramp up of the positive voltage to minimize polarization to reduce the threshold combined with a large voltage gradient to overcome the threshold.

It should be further understood that the waveforms 140-174 are each considered to be generic in the sense that the amplitudes, widths, time constants, and delays between phases may vary somewhat to provide efficacious defibrillation so long as the basic shape of the respective waveform is maintained. To demonstrate this, a detailed discussion of the waveform 140 is set forth below with reference to FIG. 32. However, it should be understood that similar statements are applicable to each of the waveforms 140-174.

Figure 32:
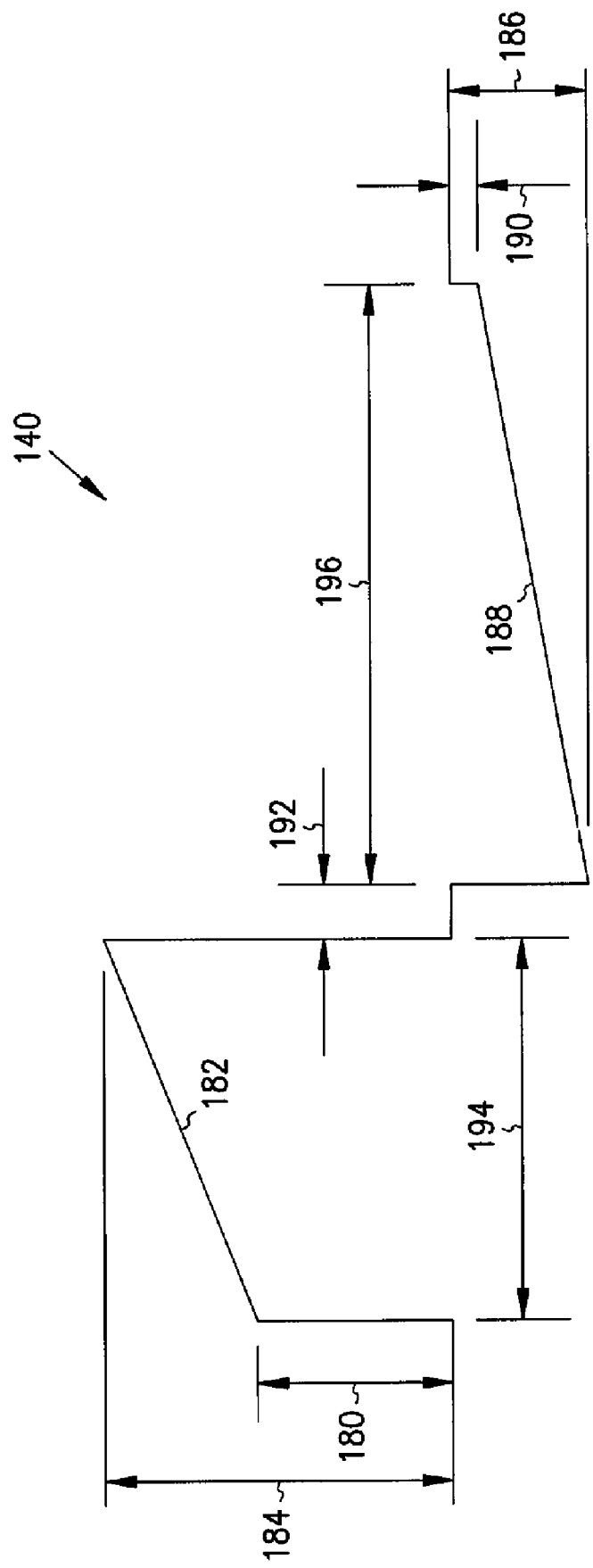
FIG. 32 illustrates a detailed version of the waveform illustrated in FIG. 14.

As illustrated in FIG. 32, the waveform 140 has an initial amplitude 180, typically between 0 volts and 50 volts. The amplitude slopes upwardly as a ramp 182 until it reaches a maximum amplitude 184, typically between about 200 volts and 400 volts, that is greater than the initial amplitude 180. Advantageously, the slope of the ramp 182 is greater than zero but need not be precisely linear, such as less than 70 volts per millisecond. At the beginning of the second phase, the waveform 140 transitions from the maximum positive amplitude 184 to the maximum negative amplitude 186, typically between about −200 volts and −400 volts. The amplitude of the waveform 140 then slopes upwardly in the form of a ramp 188 to a final negative amplitude 190, typically between 0 volts and −50 volts. Again, the slope of the ramp 188 is advantageously greater than zero but need not be precisely linear, such as less than 70 volts per millisecond.

The waveform 140 may also exhibit an interphase delay 192 that is greater than or equal to zero. Advantageously, the interphase delay 192 is as close to zero as possible, but it may have some small positive value due to the manner in which the circuit that generates the waveform 140 operates. Finally, the widths 194 and 196 of the positive and negative phases are greater than zero. Indeed, the amplitudes 180, 184, 186, and 190 and the widths 194 and 196 are typically selected to provide efficacious defibrillation while minimizing power consumption.

The waveforms 140 and 150 are of particular interest, because these waveforms along with waveforms 146, 148, 152, 158, 160, and 162, have a large gradient between the positive peak of the first phase and the negative peak of the second phase. It is currently believed that this large gradient, along with an appropriate selection of slope, promotes more effective defibrillation than other biphasic waveforms. Indeed, the results of certain tests support this belief.

During testing on eight canine subjects, it has been determined that the waveform 150 provides more efficacious defibrillation than the waveform 174. Before discussing details of this test, it should be noticed that the waveform 150 differs from the waveform 174 primarily in the positive phase.

Indeed, as illustrated, the negative phase of the waveforms 150 and 174 are identical. However, it should be noted that the positive phase of the waveform 150 begins at a nominal positive value and slopes positively to a maximum positive value before transitioning to a maximum negative value in the negative phase. In contrast, the waveform 174 includes a positive phase which begins at its maximum positive value and slopes negatively to a lower positive value before transitioning to the maximum negative value in the negative phase.

The purpose of this test was to examine the effects of rising edge waveforms on defibrillation thresholds, commonly referred to as DFT. In this test, the defibrillation efficacy of a test waveform generally corresponding to the waveform 150 was compared to a capacitive discharge reference waveform generally corresponding to the waveform 174. The reference waveform was a biphasic, truncated, capacitive discharge waveform with a first phase having a duration of 6.5 milliseconds and a second phase having a duration of 3.5 milliseconds, with a delay between phases of 0.08 milliseconds. The capacitance of both phases was fixed at 125 microfarads. In as much as the capacitance and pulse widths were fixed, the load impedance and the peak voltage of the first phase generally determine the total energy delivered in both phases.

The test waveform was a biphasic waveform having a positive first phase and a negative second phase with a delay between phases of 0.1 milliseconds. Although the rising edge waveform in the first phase differs from the capacitive discharge waveform in the second phase, the peak voltage of the negative phase was correlated as closely as possible to the peak voltage of the first phase. However, due to energy delivery considerations, the peak voltage of the negative phase was varied by as much as ±20 percent from the peak voltage of the positive phase. The negative phase of the test waveform remained identical to the negative phase of the reference waveform throughout the test. However, the duration and slope of the positive phase was varied throughout the test as set forth in the table below.

TABLE 1

BIPHASIC WAVEFORM DESIGN

| CONDITION NUMBER | SLOPE OF FIRST PHASE | PULSE WIDTH OF POSITIVE/NEGATIVE PHASE |
|---|---|---|
| 1 | 40 V/ms. | 3 ms./3.5 ms. |
| 2 | 80 V/ms. | 3 ms./3.5 ms. |
| 3 | 40 V/ms. | 4 ms./3.5 ms. |
| 4 | 80 V/ms. | 4 ms./3.5 ms. |
| 5 | 40 V/ms. | 5 ms./3.5 ms. |
| 6 | 80 V/ms. | 5 ms./3.5 ms. |

In the test, the reference waveform was used to define a reference energy corresponding to a defibrillation threshold. Once this reference energy was defined, a search algorithm applied test waveforms randomly from about 50 percent to about 200 percent of the reference energy defined by the reference waveform. When the data from the test waveforms and the reference waveform was analyzed and compared, the data clearly showed a reduction of the defibrillation threshold associated with the test waveform. Specifically, the data demonstrated that the test waveform was particularly efficacious where the peak positive voltage was greater than 300 volts with the slope less than 70 volts per millisecond. Indeed, the data demonstrated a trend for lower slope value coupled with higher peak voltages to be more efficacious for defibrillation. Overall, by proper selection of the peak voltage in the positive phase and slope value, it was found that the defibrillation threshold can be reduced significantly, as the data showed reductions of 10 percent to 50 percent as compared to the reference waveform.

Figure 33:
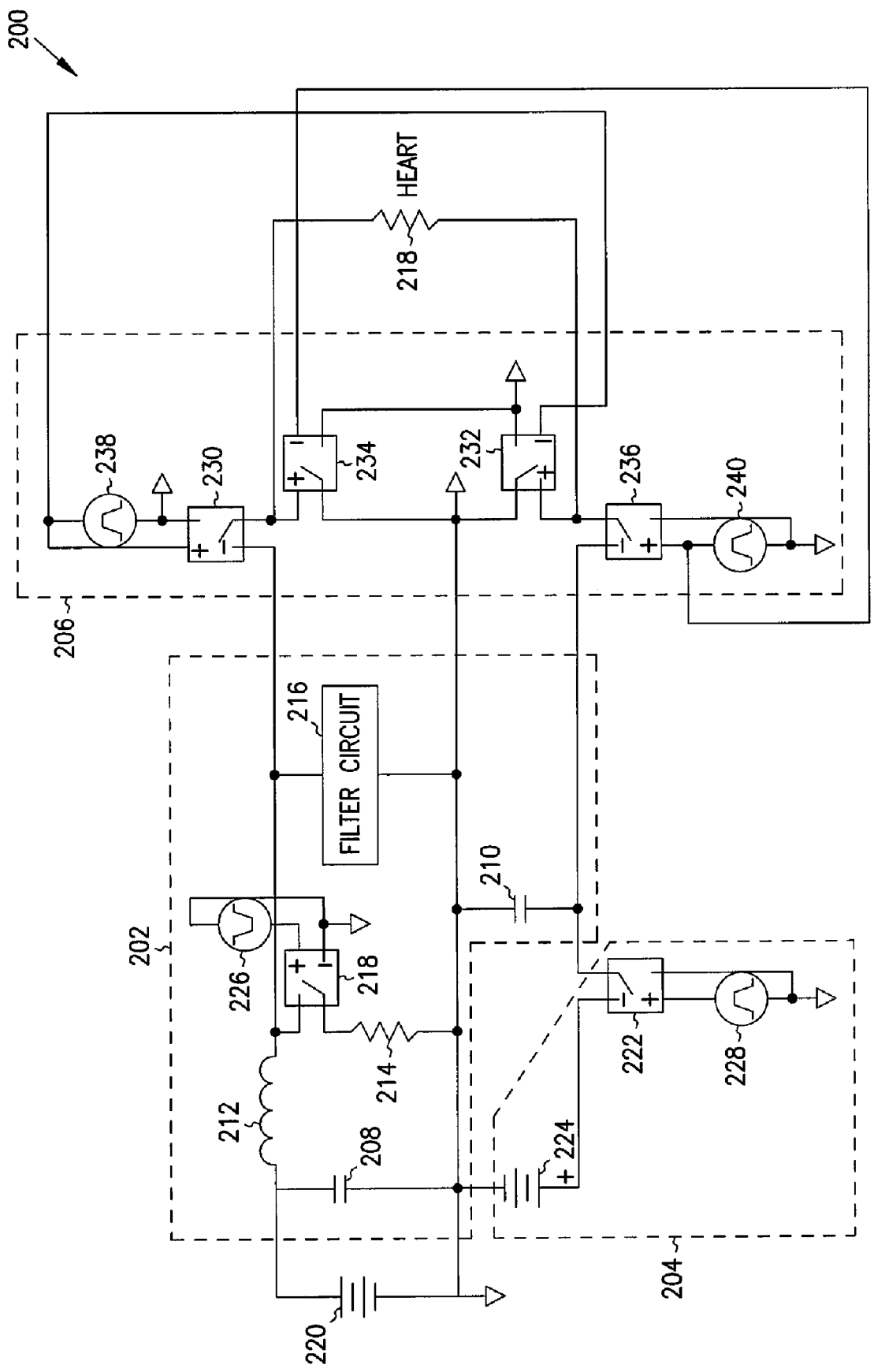
FIG. 33 illustrates a first embodiment of a circuit for generating biphasic defibrillation waveforms, such as the waveforms illustrated in FIGS. 14-31.

FIG. 33 illustrates a circuit 200 that is capable of generating the waveforms 140-174. The circuit 200 includes three subcircuits for producing the desired waveforms. The first subcircuit is a curve shaping circuit 202, the second subcircuit is a charging circuit 204, and the third subcircuit is a biphasic switching circuit 206.

In regard to the curve shaping circuit 202, the values of the capacitors 208 and 210, the inductor 212, and the resistor 214 are chosen to produce the desired discharge curve which corresponds to the sloped portions 104, 108, 112, 116, 120, 124, 128, 132, and 136 of the respective waveforms 102, 106, 110, 114, 118, 122, 126, 130, and 134. For example, the values of the inductor 212 and the capacitor 208 can be modified to produce the waveforms 148 and 152. The resistor 214 essentially operates as a "dummy" load which is used to modify the discharge characteristics of the capacitor 208. Finally, the filter circuit 216, which is typically a capacitive circuit, may be used to linearize the discharge output to form ramped sections as illustrated in the waveforms 102, 114, and 118, for example. Even more particularly, it should be understood that the resistance 218 provided by the heart along with the values of the capacitor 208 and the inductor 212 generally determine the initial shape of the waveform. While the resistor 214 may be used to change the waveform shape, it should also be noted that changes in the value of the capacitor 208 or the value of the inductor 212, whether by using variable elements, parallel elements, or elements of different values, may also affect the waveform shape.

To charge the elements in the curve shaping circuit 202, the switch 218 is initially placed in an open state so that the power supply 220 can charge the capacitor 208. Similarly, the charging circuit 204 closes the switch 222 so that the power supply 224 can charge the capacitor 210. In this embodiment the state of the switches 218 and 222 are controlled by pulse generators 226 and 228, respectively. However, it should be understood that the switches 218 and 222 alternatively may be controlled by a variety of other suitable methods, such as an appropriate logic circuit, state machine, or microprocessor.

Once the capacitors 208 and 210 have been charged, the switches 218 and 222 are simultaneously opened to allow the respective capacitors 208 and 210 to discharge. To produce the positive voltage of the first phase of the biphasic waveform, the switches 230 and 232 of the switching circuit 206 are closed, and the switches 234 and 236 are opened. As before, the state of the switches in the charging circuit 206 are controlled by pulse generators 238 and 240, but other methods of control may be suitable.

With the switches 230-236 in this configuration, current flows through the switch 230, through the heart 218, and through the switch 232 to complete the circuit. This current is designated as the first phase current which produces the positive voltage waveform in the heart 218. To complete phase one and begin phase two, the switches 230 and 232 are opened, and the switches 234 and 236 are closed. With the switches in this configuration, current flows through the switch 236, through the heart 218, and through the switch 234 to complete the circuit. This phase two current produces the negative voltage waveform in the heart 218.

Although the circuit 200 is capable of producing any of the biphasic waveforms 140-174 illustrated in FIGS. 14-31, it does suffer from certain disadvantages. First, the circuit 200 includes at least one inductor 212. Because it is difficult, if not commercially impossible, to fabricate an inductor of sufficient value to produce the necessary waveform while still being small enough to fit within an implantable cardiac stimulator, the circuit 200 may not be suitable for an implantable device. Secondly, without the use of multiple elements 208-214 and/or variable elements 208-214, the circuit 200 can only produce a waveform having a specified shape. Even if multiple or variable elements were used, these elements would occupy even more space, making the circuit 200 even less suitable for an implantable device.

Figure 34:
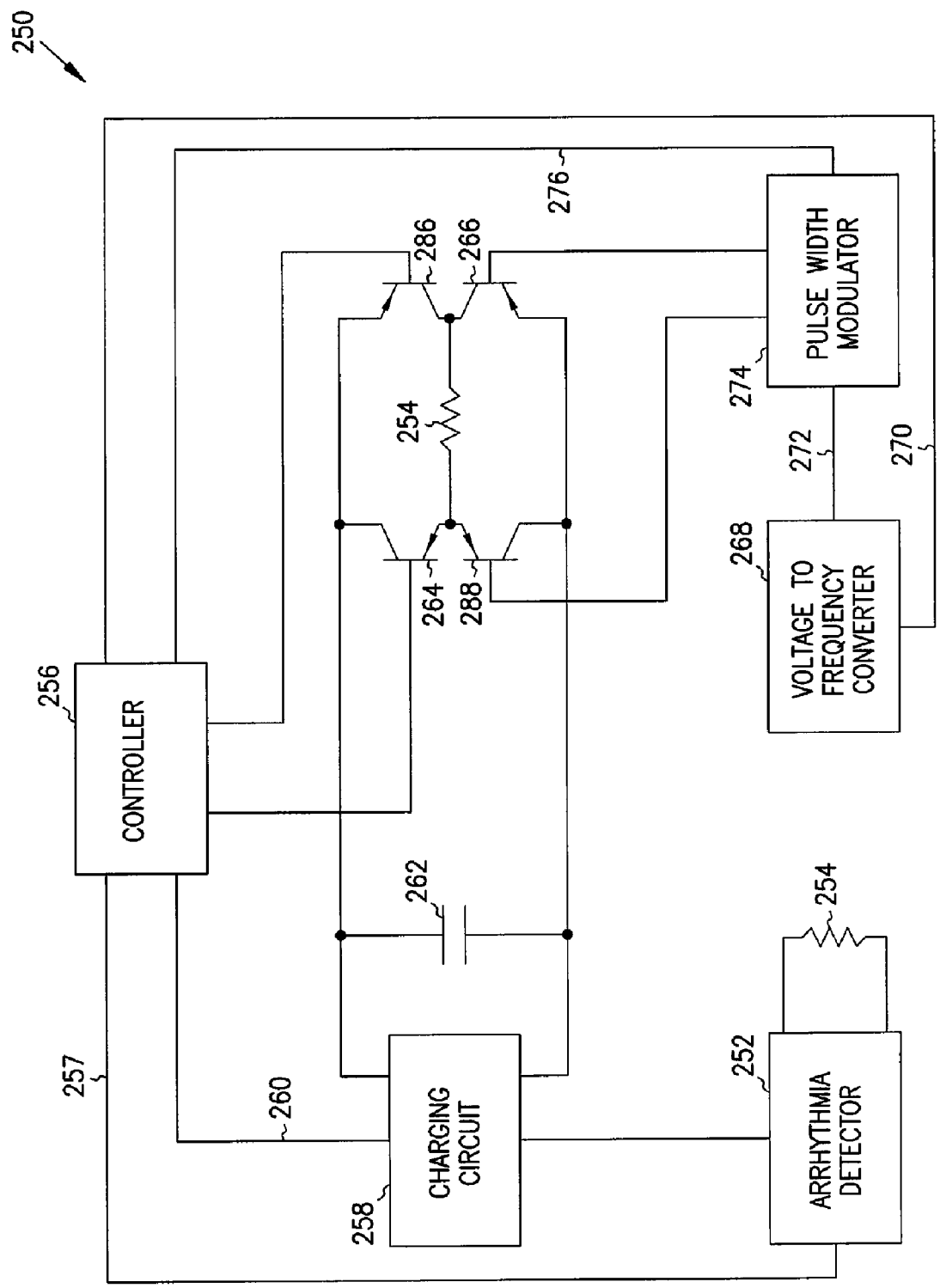
FIG. 34 illustrates a second embodiment of a circuit for generating biphasic defibrillation waveforms, such as the waveforms illustrated in FIGS. 14-31.
Figure 35:
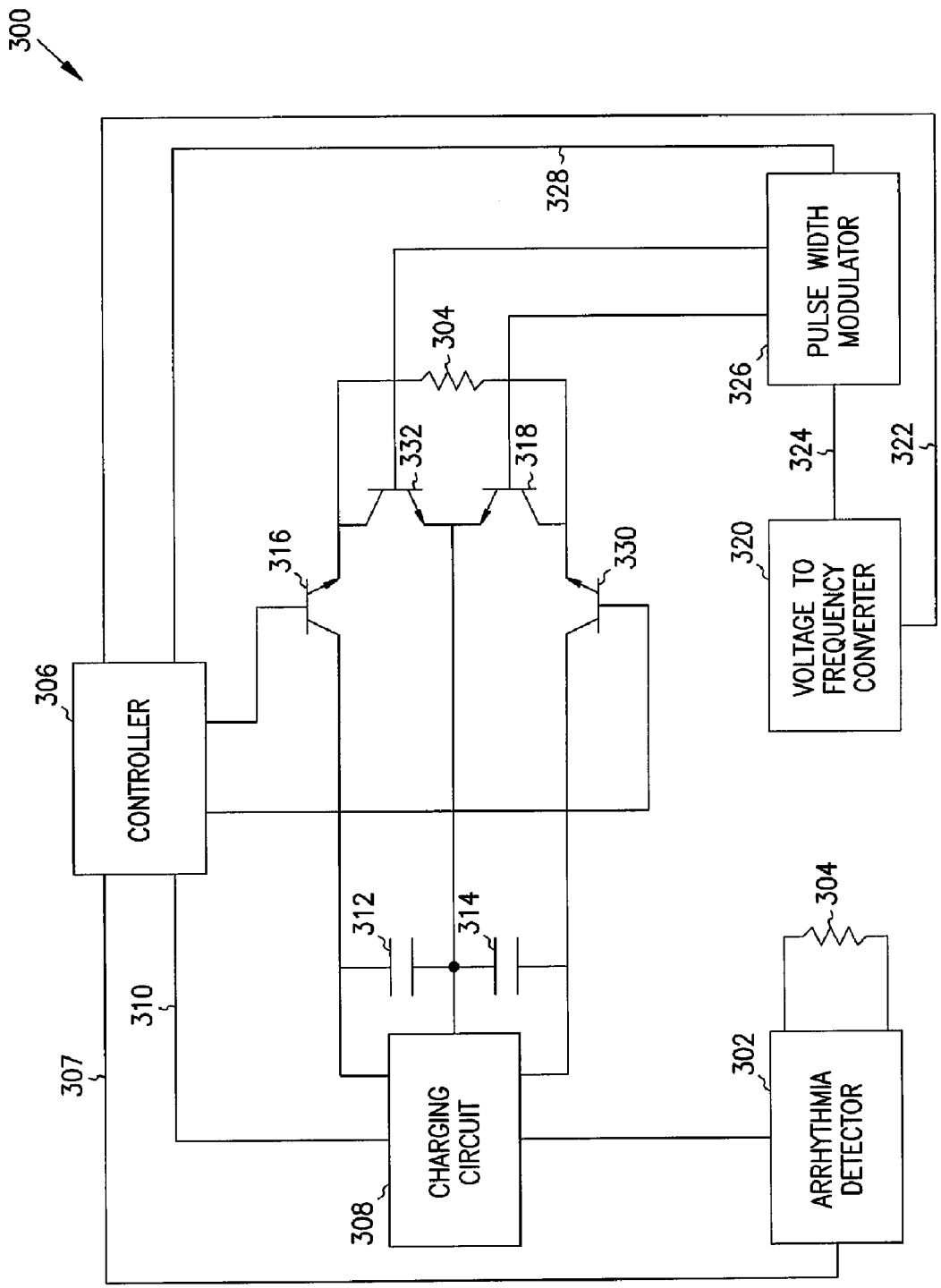
FIG. 35 illustrates a third embodiment of a circuit for generating biphasic defibrillation waveforms, such as the waveforms illustrated in FIGS. 14-31.

The circuits 250 and 300 illustrated in FIGS. 34 and 35 have been designed to address these problems. The circuits 250 and 300 use a combination of pulse width modulation (PWM) and frequency modulation (FM) to generate a plurality of waveforms suitable for defibrillating ventricular or atrial tissue. Through the proper choice of these PWM and FM parameters, and through the proper selection of capacitor charging parameters, the circuits 250 and 300 can generate a number of suitable monophasic or biphasic waveforms such as the waveforms 140-174. Particularly, the circuits 250 and 300 can produce a rising edge waveform that begins at some value greater than or equal to zero volts and increases linearly to some maximum voltage dependent upon the slope and duration of the first phase. The circuits 250 and 300 can also produce, in a similar manner, a second phase waveform where the initial voltage is dependent upon the final voltage of the capacitor used to generate the first phase (circuit 250 of FIG. 34) or upon the charge voltage of a second capacitor (circuit 300 of FIG. 35).

In regard to the circuit 250 illustrated in FIG. 34, an arrhythmia detector 252 is coupled to the heart which is symbolized by a resistance 254. If the arrhythmia detector 252 detects a treatable arrhythmia in the heart 254, it issues a command to the system controller 256 via a line 257. The system controller 256, typically the microprocessor 32, signals a charging circuit 258 via a line 260 to initiate the charging of a capacitor 262. The charging circuit 258 then charges the capacitor 262 to a preprogrammed voltage. When the capacitor 262 reaches the desired voltage level, the system controller 256 closes a switch 264 and modulates the opening and closing of a switch 266 to control delivery of a defibrillation signal to the heart. The controller 256 controls the modulation of the switch 266 by delivering a signal on line 270 to a voltage-to-frequency converter 268. The magnitude of the voltage delivered to the voltage-to-frequency converter 268 by the controller 256 controls the frequency of the signal delivered by the voltage-to-frequency converter 268 on line 272. The frequency is advantageously in a range between about 5 kilohertz and about 25 kilohertz. A pulse width modulator 274 receives the frequency signal from the line 272, and it also receives a control signal from the controller 256 via line 276. The pulse width modulator 274 delivers a pulse width modulated signal to the switch 266. The frequency of the pulse width modulated signal is controlled by the frequency of the signal on line 272, while the duty cycle of the pulse width modulated signal is controlled by the control signal delivered on line 276. Each time the pulse width modulated signal is high, the switch 266 closes so that current passes from the capacitor 262 through the switch 264, through the heart 254, and through the switch 266 to complete the circuit. Thus, the waveforms are produced by essentially modulating the current discharged by the capacitor 262.

Figure 36:
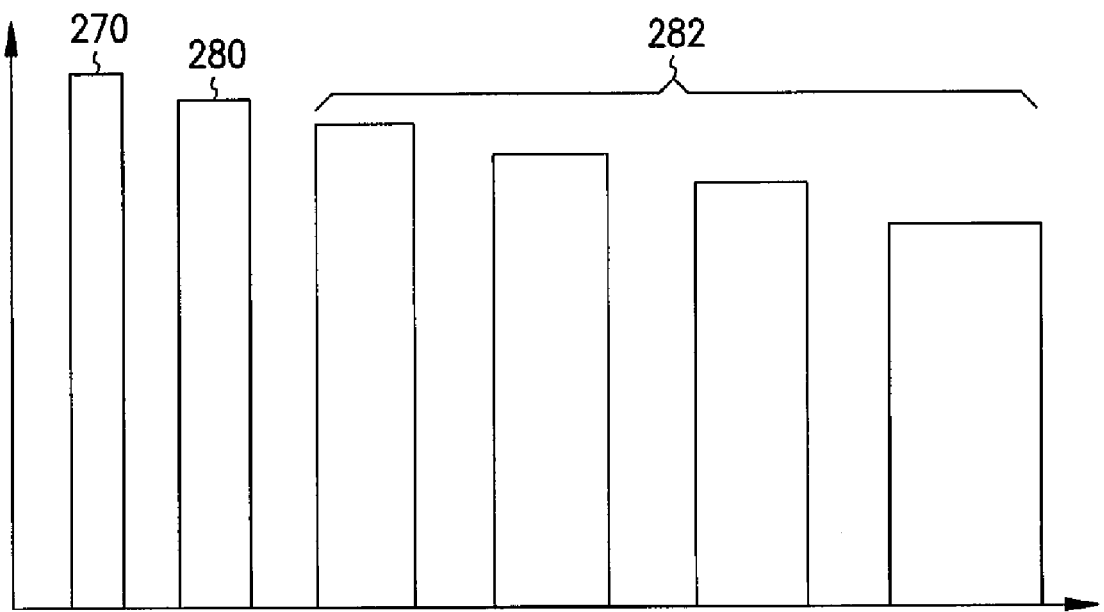
FIG. 36 illustrates a pulse train generated by the circuit illustrated in FIG. 34.
Figure 37:
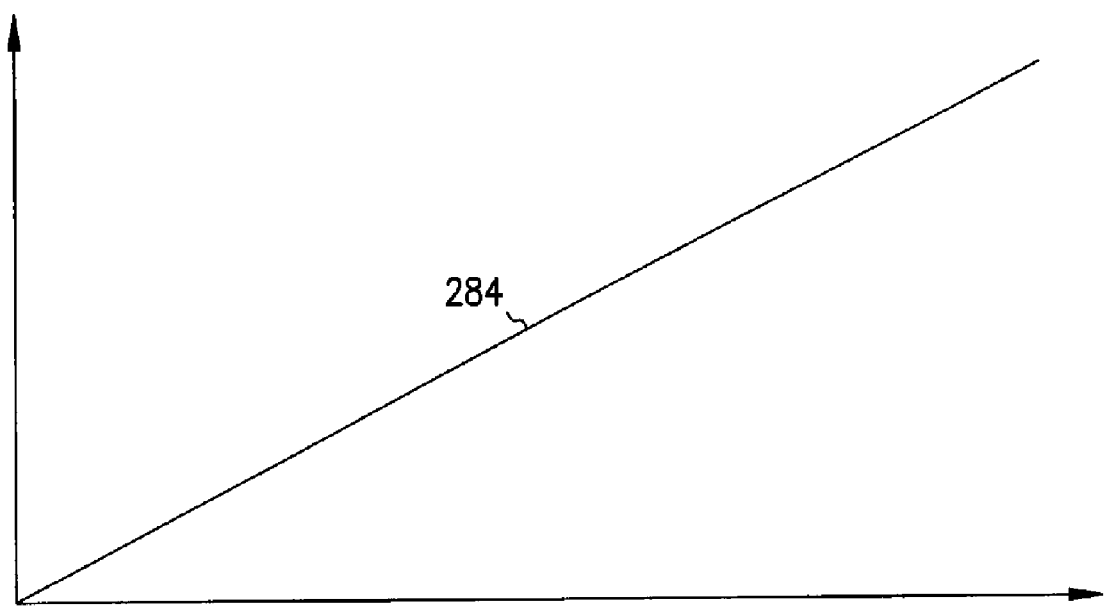
FIG. 37 illustrates a waveform in the heart produced by the pulse train illustrated in FIG. 36.

An example of actual waveform characteristics is illustrated in FIG. 36. Here, it can be seen that the first pulse 278 of the waveform has a voltage magnitude equal to the fully charged voltage of the capacitor 262, with the pulse width determined by the duty cycle of the pulse width modulated signal delivered to the switch 266. The next pulse 280 has a lower magnitude because the capacitor 262 was partially discharged in order to form the first pulse 278. As before, the width of the second pulse 280 is determined by the duty cycle of the pulse width modulated signal delivered to the switch 266. Furthermore, the time delay between the first pulse 278 and the second pulse 280 is determined by the frequency of the pulse width modulated signal delivered to the switch 266. As successive pulses 282 are delivered, the magnitude of each pulse tends to diminish as the capacitor 262 continues to discharge. The duty cycle of the pulse width modulated signal continues to determine the width of each successive pulse 282, while the frequency of the pulse width modulated signal continues to determine the time at which each pulse edge occurs.

Each of these pulses is applied to the heart via the path described above. Notwithstanding the fact that the heart 254 has been illustrated by a resistor, it is believed that myocardial tissue and individual cells essentially act as low pass filters in the sense that they reject frequencies higher than approximately two kilohertz to about five kilohertz. In other words, the heart 254 does not respond to each pulse so long as the pulses are being applied to it at a suitably high frequency. Instead, the heart tends to filter the pulses and integrate the power in the pulse train. Thus, the pulse train illustrated in FIG. 36 will generate a voltage through the heart similar to the waveform 284 illustrated in FIG. 37. However, it should be understood that by varying the timing and width of the pulse train virtually any waveform can be created by the circuit 250.

Phase two of a biphasic waveform is produced by the circuit 250 in much the same way as the phase one component of the waveform. Specifically, upon completion of the phase one component, the controller 256 opens the switches 264 and 266, closes the switch 286, and modulates the opening and closing of the switch 288. Similar to the operation described above, the switch 286 remains on at all times during phase two, while the switch 288 receives a pulse width modulated signal from the pulse width modulator 274. The controller 256 controls the pulse width modulated signal in the same manner as described previously in order to produce the desired shape of the phase two component of the waveform. Hence, current flows from the capacitor 262 through the switch 286, through the heart 254, and through the switch 288 to complete the circuit.

The operation of the circuit 300 illustrated in FIG. 35 is similar to the operation of the circuit 250 described above, with the primary exception of the use of a dedicated capacitor to generate each respective phase of the biphasic waveform. As illustrated in FIG. 35, an arrhythmia detector 302 is coupled to the heart which is symbolized by a resistance 304. If the arrhythmia detector 302 detects a treatable arrhythmia in the heart 304, it issues a command to the system controller 306 via a line 307. The system controller 306 signals a charging circuit 308 via a line 310 to initiate the charging of the capacitors 312 and 314. The charging circuit 308 then charges the capacitors 312 and 314 to a respective preprogrammed voltage. When the capacitors 312 and 314 reach the desired voltage levels, the system controller 306 closes a switch 316 and modulates the opening and closing of a switch 318. The controller 306 controls the modulation of the switch 318 by delivering a signal to a voltage-to-frequency converter 320 on line 322. The magnitude of the voltage delivered to the voltage-to-frequency converter 320 by the controller 306 controls the frequency of the signal delivered by the voltage-to-frequency converter 320 on line 324. The frequency is advantageously in a range between about 5 kilohertz and about 25 kilohertz. A pulse width modulator 326 receives the frequency signal from the line 324, and it also receives a control signal from the controller 306 via line 328. The pulse width modulator 326 delivers a pulse width modulated signal to the switch 318. The frequency of the pulse width modulated signal is controlled by the frequency of the signal on line 324, while the duty cycle of the pulse width modulated signal is controlled by the control signal delivered on line 328. Each time the pulse width modulated signal is high, the switch 318 closes so that current passes from the capacitor 312 through the switch 316, through the heart 304, and through the switch 318 to complete the circuit.

The negative phase of a biphasic waveform is produced by the circuit 300 in much the same way as the positive phase component of the waveform. Specifically, upon completion of the phase one component, the controller 306 opens the switches 316 and 318, closes the switch 330, and modulates the opening and closing of the switch 332. Similar to the operation described above, the switch 330 remains closed at all times during phase two, while the switch 332 receives a pulse width modulated signal from the pulse width modulator 326. The controller 306 controls the pulse width modulated signal in the same manner as described previously in order to produce the desired shape of the phase two component of the waveform. However, unlike the circuit 250, in the circuit 300 current flows from the second capacitor 314 through the switch 330, through the heart 304, and through the switch 332 to complete the circuit. Thus, the negative phase is not reliant on the charge left in the first capacitor 312 at the end of the positive phase.

Specific embodiments of the invention have been shown by way of example in the drawings and have been described in detail herein. However, the invention may be susceptible to various modifications and alternative forms, and it should be understood that the invention is not intended to be limited to the particular forms disclosed. Rather, the invention is to cover all modifications, equivalents, and alternatives falling within the spirit and scope of the invention as defined by the appended claims.

What is claimed is:

1. A defibrillator comprising:
a biphasic voltage waveform generator circuit, the circuit generating a waveform that includes:
a positive voltage phase beginning at about zero volts and having an initial positive voltage magnitude greater than zero volts, the positive voltage phase having a first negatively sloped portion extending from the initial positive voltage magnitude to a terminal positive voltage magnitude less than the initial positive voltage magnitude; and
a negative voltage phase having an initial negative voltage magnitude less than or equal to zero volts extending from the terminal positive voltage magnitude of the positive voltage phase, the negative voltage phase having a second negatively sloped portion extending from the initial negative voltage magnitude to a terminal negative voltage magnitude less than or equal to zero volts.

2. The defibrillator of claim 1, wherein the positive phase waveform shape is independently selectable from a first set of waveform shapes.

3. The defibrillator of claim 2, wherein the negative phase waveform shape is independently selectable from a second set of waveform shapes.

4. The defibrillator of claim 1, wherein the negative phase waveform shape is independently selectable from a second set of waveform shapes.

5. The defibrillator of claim 1, wherein the first negatively sloped portion comprises a substantially linear slope.

6. The defibrillator of claim 1, wherein the second negatively sloped portion comprises a substantially linear slope.

7. The defibrillator of claim 1, wherein the first negatively sloped portion comprises a continuously increasing slope.

8. The defibrillator of claim 1, wherein the second negatively sloped portion comprises a continuously increasing slope.

9. The defibrillator of claim 1, wherein the first negatively sloped portion comprises a continuously decreasing slope.

10. The defibrillator of claim 1, wherein the second negatively sloped portion comprises a continuously decreasing slope.

11. The defibrillator of claim 1, wherein the waveform includes an interphase delay between the positive voltage phase and the negative voltage phase.

12. A defibrillator comprising:
a biphasic voltage waveform generator circuit, the circuit generating a waveform that includes:
a positive voltage phase beginning at about zero volts and having an initial positive voltage magnitude greater than zero volts, the positive voltage phase having a first negatively sloped portion extending from the initial positive voltage magnitude to a terminal positive voltage magnitude less than the initial positive voltage magnitude, the first negatively sloped portion comprising a substantially linear slope; and
a negative voltage phase having an initial negative voltage magnitude less than or equal to zero volts extending from the terminal positive voltage magnitude of the positive voltage phase, the negative voltage phase having a second negatively sloped portion extending from the initial negative voltage magnitude to a terminal negative voltage magnitude less than or equal to zero volts.

13. The defibrillator of claim 12, wherein the negative phase waveform shape is independently selectable from a set of waveform shapes.

14. The defibrillator of claim 12, wherein the second negatively sloped portion comprises a substantially linear slope.

15. The defibrillator of claim 12, wherein the second negatively sloped portion comprises a continuously increasing slope.

16. The defibrillator of claim 12, wherein the second negatively sloped portion comprises a continuously decreasing slope.

17. A method of generating a biphasic defibrillation waveform comprising:
generating a positive voltage phase having an initial positive voltage having a magnitude greater than zero volts and having a first negatively sloped portion extending from the initial positive voltage to a terminal positive voltage having magnitude greater than or equal to zero volts; and
generating a negative voltage phase having an initial negative voltage having a magnitude less than or equal to zero volts extending from the terminal positive voltage of the positive voltage phase, the negative voltage phase having a second negatively sloped portion extending from the initial negative voltage to a terminal negative voltage having a magnitude less than or equal to zero volts.

18. The method of claim 17, wherein generating the positive voltage phase includes independently selecting the positive phase waveform shape from a first set of waveform shapes.

19. The method of claim 17, wherein generating the negative voltage phase includes independently selecting the negative phase waveform shape from a second set of waveform shapes.

20. A method of generating a biphasic defibrillation waveform comprising:

generating a positive voltage phase having an initial positive voltage having a magnitude greater than zero volts and having a first negatively sloped portion extending from the initial positive voltage to a terminal positive voltage having magnitude greater than or equal to zero volts, the first negatively sloped portion comprising a substantially linear slope; and generating a negative voltage phase having an initial negative voltage having a magnitude less than or equal to zero volts extending from the terminal positive voltage of the positive voltage phase, the negative voltage phase having a second negatively sloped portion extending from the initial negative voltage to a terminal negative voltage having a magnitude less than or equal to zero volts.

21. The method of claim 20, wherein generating the negative voltage phase includes independently selecting the negative phase waveform shape from a set of waveform shapes.

* * * * *